United States Patent
Kim et al.

(10) Patent No.: US 6,437,140 B1
(45) Date of Patent: Aug. 20, 2002

(54) PROCESS FOR PREPARING ETHYL 3-(2,5,6-TRIHALOPYRIDIN-3-YL)-3-OXOPROPIONATE FROM 2,5,6-TRIHALO-3-CYANOPYRIDINE

(75) Inventors: Youn Ok Kim, Daejeon; Suk Keun Chun, Kyeonggi-do; Jae Eun Lee, Incheon, all of (KR)

(73) Assignee: Fusion Chem Tech Co., Ltd. (KR)

( * ) Notice: Subject to any disclaimer, the term of this patent is extended or adjusted under 35 U.S.C. 154(b) by 0 days.

(21) Appl. No.: 09/990,800

(22) Filed: Nov. 14, 2001

(51) Int. Cl.⁷ .............................................. C07D 213/55
(52) U.S. Cl. ....................... 546/341; 546/345
(58) Field of Search .................. 546/341, 345

(56) References Cited

FOREIGN PATENT DOCUMENTS

JP          3-74231        9/1995

OTHER PUBLICATIONS

Urban, F.J. et al., "An alternative synthesis of ethyl 3–(2–chloro–4,5–difluorophenyl)–3–oxopropionate and ethyl 3–(2,6–dichloro–5–fluoropyridin–3–yl)–3–oxopropionate" *OPPI Briefs*, 1997, 29(2), pp. 231–234.

*Primary Examiner*—Patricia L. Morris
(74) *Attorney, Agent, or Firm*—Woodcock Washburn LLP

(57) ABSTRACT

The new process for preparing ethyl 3-(2,5,6-trihalopyridin-3-yl)-3-oxopropionate from 2,5,6-trihalo-3-cyanopyridine in accordance with the present invention comprises reacting 2,5,6-trihalo-3-cyanopyridine with ethyl haloacetate at the presence of a transition metal in powder in anhydrous solvent, and treating the resulting solution with HCl. In particular, the new process for preparing ETPO from THCP comprises heating 2,5,6-trihalo-3-cyanopyridine and a transition metal in powder in anhydrous solvent to the boiling point, reacting 2,5,6-trihalo-3-cyanopyridine with ethyl haloacetate by adding ethyl haloacetate dropwise to the resulting solution, cooling the resulting solution to about 10° C., adding concentrated HCl and distilled water to the resulting solution during agitation thereof, and filtering the product.

15 Claims, No Drawings

PROCESS FOR PREPARING ETHYL 3-(2,5,6-TRIHALOPYRIDIN-3-YL)-3-OXOPROPIONATE FROM 2,5,6-TRIHALO-3-CYANOPYRIDINE

FIELD OF THE INVENTION

The present invention relates to a new process for preparing ethyl 3-(2,5, 6-trihalopyridin-3-yl)-3-oxopropionate (hereinafter "ETPO") which is usable as an intermediate of a quinolinic antibiotic. More particularly, the present invention relates to a new process for preparing ETPO from 2,5,6-trihalo-3-cyanopyridine (hereinafter "THCP") using a transition metal and ethyl haloacetate.

BACKGROUND OF THE INVENTION

Ethyl 3-(2,5,6-trihalopyridin-3-yl)-3-oxopropionate which is usable as an intermediate of a quinolinic antibiotic is represented as the following formula:

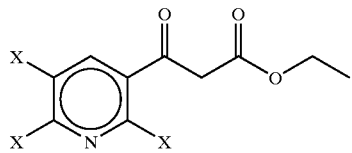

ETPO [Ethyl 3-(2,5,6-trihalopyridin-3-yl)-3-oxopropionate]

where X is a halogen atom such as F, Cl, Br or I.

It has been known a method of synthesizing ETPO in Japanese Patent Pulication Number 3-74231 published Nov. 26, 1991. The method of the Japanese Patent is to prepare ETPO from THCP through 4 steps process of hydration, chlorination, alkylation and dealkoxycarbonylation. The reaction scheme are shown as follow:

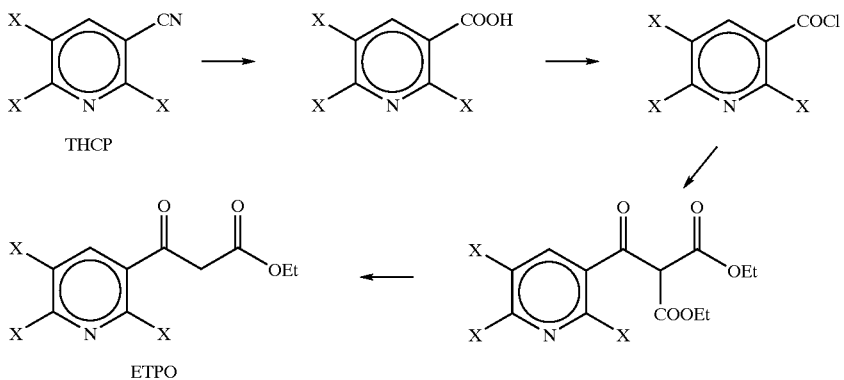

The method of ETPO above according to the Japanese Patent has a lower yield in total such as 13%, because the method is carried out through 4 steps. Furthermore, the method is not economical in terms of the cost of preparation. In particular, the method is not practical, because the yield at the last step of dealkoxycarbonylation is very low and the method is not reproducible.

In order to overcome the disadvantages of the method of the Japanese Patent, Pfizer Inc. developed in 1997 a new method using ethyl acetoacetate as alkylation agent instead of diethyl malonate that had been used in the Japanese Patent. The reaction scheme of the method by Pfizer Inc. is represented as follow:

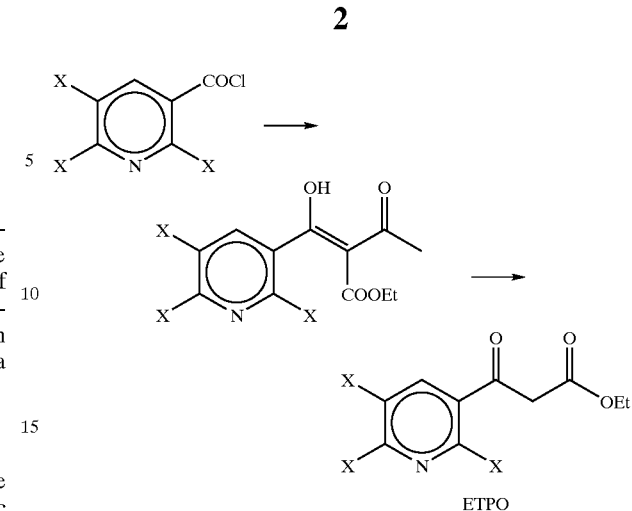

However, the method by Pfizer Inc. failed to increase the total yield, which turns out 14% approximately.

As discussed above, both the method of the Japanese Patent and the method of Pfizer Inc. failed to increase the total yield in the preparation of ETPO. The preparation of ETPO in a low total yield means that ETPO cannot be prepared due to the high cost.

The present inventors have developed a new process for preparing ETPO from THCP in one step process using a transition metal and ethyl haloacetate, which can prepare ETPO having higher yield and purity compared to the ETPOs synthesized by a conventional method.

OBJECTS OF THE INVENTION

A feature of the present invention provides a new method of preparing ETPO from THCP in one step process using a transition metal and ethyl haloacetate.

Another feature of the present invention provides a method of preparing ETPO from THCP, the yield after recrystallization being about 80% or more.

A further feature of the present invention provides a method of preparing ETPO from THCP, the purity after recrystallization being about 97% or more.

A further feature of the present invention provides a method of preparing ETPO from THCP, which is economical in cost of preparation and has a good productivity by preparing ETPO having a yield of about 80% or more and a purity of about 97% or more after recrystallization.

Other objects and advantages of this invention will be apparent from the ensuing disclosure and appended claims.

SUMMARY OF THE INVENTION

The new process for preparing ethyl 3-(2,5,6-trihalopyridin-3-yl)-3-oxopropionate from 2,5,6-trihalo-3-cyanopyridine in accordance with the present invention comprises reacting 2,5,6-trihalo-3-cyanopyridine with ethyl haloacetate at the presence of a transition metal in powder in anhydrous solvent, and treating the resulting solution with HCl.

In particular, the new process for preparing ETPO from THCP comprises heating 2,5,6-trihalo-3-cyanopyridine and a transition metal in powder in anhydrous solvent to the boiling point, reacting 2,5,6-trihalo-3-cyanopyridine with ethyl haloacetate by adding ethyl haloacetate dropwise to the resulting solution, cooling the resulting solution to about 10° C., adding concentrated HCl and distilled water to the resulting solution during agitation thereof, and filtering the product.

The ETPO obtained in accordance with the present invention has a yield of about 80% or more and a purity of about 97% or more after recrystallization.

DETAILED DESCRIPTION OF THE INVENTION

According to the present invention, ethyl 3-(2,5,6-trihalopyridin-3-yl)-3-oxopropionate is directly prepared in one step process compared to the conventional processes from the starting material of 2,5,6-trihalo-3-cyanopyridine. First, THCP is reacted with ethyl haloacetate at the presence of a transition metal in powder in anhydrous solvent, and the resulting solution is treated with concentrated HCl solution. Then the resulting solution is filtered and the filtrates are recrystallized to produce ETPO having high purity. The reaction for preparation of ETPO in accordance with the present invention is represented as follow:

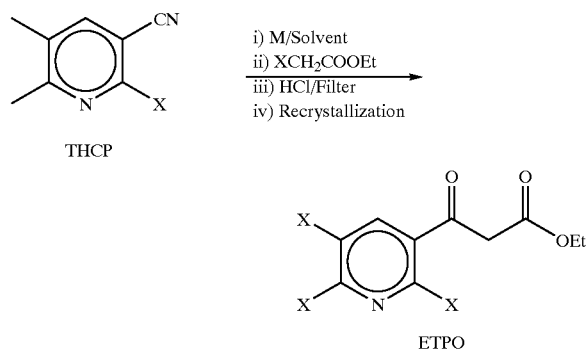

where X is a halogen atom and M is a transition metal.

More particularly, a transition metal in powder and THCP are added to anhydrous solvent and the resulting solution is heated to the boiling point. Particular preferred examples of anhydrous solvent according to the present invention include anhydrous tetrahydrofuran (THF) and anhydrous diethyl ether. Particular preferred examples of transition metal according to the present invention include Mg Zn, Sn, Pb, Cu, Ag, Ni and Co. The transition metal in the state of powder can be preferably used. The transition metal powder is preferably activated at 0–30° C. Before heating the resulting solution, the activated transition metal powder and THCP are under reduced pressure or vacuum to evaporate moisture and solvent, and then nitrogen gas is filled. To the reactor is anhydrous solvent added and the resulting solution is heated to the boiling point.

To the heated solution is ethyl haloacetate dropwise added to react THCP with ethyl haloacetate by adding ethyl haloacetate. Particular preferred examples of ethyl haloacetate include ethyl chloroacetate, ethyl bromoacetate, and ethyl iodoacetate. The ethyl haloacetate is dropwise added over about 1–3 hours. After the ethyl haloacetate is dropwise added, the resulting solution is fluxed for about 30 minutes to about 1 hour to react further THCP with ethyl haloacetate.

The resulting solution is cooled to about 10° C., and concentrated HCl and distilled water are added to the cooled solution during agitation. The resulting solution is agitated for about 2 hours.

The agitated product is filtered to obtain unpurified ETPO in a yield of about 90% or more. The filtrate is washed within short time by putting into solvent. Cool ethanol, THF or ethyl acetate is preferably used as the solvent. The washed filtrate is put into solvent and heated to 60° C. to dissolve. The solvent is distilled and the product is quenched to obtain ETPO through recrystallization. The reflux, cooling, agitation, filtration and recrystallization above according to the present invention are easily carried out by an ordinary person in the art to which the present invention pertains. During the recrystallization, the solvent used to wash the filtrate is preferably collected and recycled with the solvent of other batches to obtain additional ETPO.

The unpurified ETPO is recrystallized using solvent to obtain purified ETPO having a high yield of about 80% or more in a yield of about 90% or more.

The invention may be better understood by the reference to the following examples which are intended for the purpose of illustration and are not to be construed as in any way limiting the scope of the present invention, which is defined in the claims appended hereto. In the following examples, all parts and percentage are by weight unless otherwise indicated.

EXAMPLES

Example 1

Magnesium powder of 1.5 mol (36g) activated at 15° C. and THCP of 1.0 mol (191 g) were added to a reactor. The reactor was kept under reduced pressure to eliminate completely moisture and solvent and was filled with nitrogen gas. To the reactor was 500 ml of THF added and the resulting solution was heated to the boiling point. To the reactor was ethyl chloroacetate of 1.5 mol (184 g) added dropwise over 2 hours. The resulting solution was refluxed for 30 minutes. and cooled to 10° C. To the reactor was 134 g of concentrated HCl added slowly and 1400 ml of distilled water added. The resulting solution was further agitated for 2 hours and filtered. The filtrate was washed within short time with cold THF of 200 ml to obtain 235 g of ETPO in a yield of 85%. The washed filtrate was put into 300 ml of THF and the resulting solution was heated to 60° C. to dissolve the filtrate completely. THF of 100 ml was distilled from the resulting solution. The resulting solution was quenched to recrystallize ETPO. 235 g of ETPO having a purity of 97% was obtained in a yield of 85%.

Example 2

Magnesium powder of 1.5 mol (36 g) activated at room temperature and THCP of 1.0 mol (191 g) were added to a reactor. The reactor was kept under reduced pressure to eliminate completely moisture and solvent and was filled with nitrogen gas. To the reactor was 500 ml of THF added and the resulting solution was heated to the boiling point. To the reactor was ethyl bromoacetate of 1.5 mol (184 g) added dropwise over 2 hours. The resulting solution was refluxed for 30 minutes, and cooled to 10° C. To the reactor was 134 g of concentrated HCl added slowly and 1400 ml of distilled water added. The resulting solution was further agitated for 2 hours and filtered. The filtrate was washed within short time with cold ethanol of 200 ml to obtain 229 g of ETPO in a yield of 82%. The washed filtrate was put into 300 ml of ethanol and the resulting solution was heated to 60° C. to dissolve the filtrate completely. Ethanol of 100 ml was distilled from the resulting solution. The resulting solution was quenched to recrystallize ETPO. 229 g of ETPO having a purity of 98% was obtained in a yield of 82%.

Example 3

Tin (Sn) powder of 1.2 mol (78 g) activated at 10° C. and THCP of 1.0 mol (191 g) were added to a reactor. The reactor was kept under reduced pressure to eliminate completely moisture and solvent and was filled with nitrogen gas. To the reactor was 500 ml of anhydrous diethyl ether added and the resulting solution was heated to the boiling point. To the reactor was ethyl chloroacetate of 1.2 mol (147 g) added dropwise over 2 hours. The resulting solution was refluxed for 30 minutes, and cooled to 0° C. To the reactor was 134 g of concentrated HCl added slowly and 1400 ml of distilled water added. The resulting solution was further agitated for 2 hours and filtered. The filtrate was washed within short time with cold iso-propanol of 200 ml to obtain 240 g of ETPO in a yield of 86%. The washed filtrate was put into 300 ml of iso-propanol and the resulting solution was heated to 75° C. to dissolve the filtrate completely. Iso-propanol of 100 ml was distilled from the resulting solution. The resulting solution was quenched to recrystallize ETPO. 240 g of ETPO having a purity of 97% was obtained in a yield of 86%.

Example 4

Copper (Cu) powder of 1.2 mol (76 g) activated at room temperature and THCP of 1.0 mol (191 g) were added to a reactor. The reactor was kept under reduced pressure to eliminate completely moisture and solvent and was firled with nitrogen gas. To the reactor was 500 ml of THF added and the resulting solution was heated to the boiling point. To the reactor was ethyl iodoacetate of 1.2 mol (257 g) added dropwise over 2 hours. The resulting solution was refluxed for 30 minutes, and cooled to 10° C. To the reactor was 134 g of concentrated HCl added slowly and 1400 ml of distilled water added. The resulting solution was further agitated for 2 hours and filtered. The filtrate was washed within short time with cold ethyl acetate of 200 ml to obtain 242 g of ETPO in a yield of 87%. The washed filtrate was put into 300 ml of ethyl acetate and the resulting solution was heated to 60° C. to dissolve the filtrate completely. Ethyl acetate of 100 ml was distilled from the resulting solution. The resulting solution was quenched to recrystallize ETPO. 242 g of ETPO having a purity of 97% was obtained in a yield of 87%.

The present invention provides a new method of preparing ETPO from THCP in one step process using a transition metal and ethyl haloacetate, which is economical in cost of preparation and has a good productivity by preparing ETPO having a yield of about 80% or more and a purity of about 97% or more after recrystallization.

The present invention can be easily carried out by an ordinary skilled person in the art. Many modifications and changes may be deemed to be with the scope of the present invention as defined in the following claims.

What is claimed is:

1. A process for preparing ethyl 3-(2,5,6-trihalopyridin-3-yl)-3-oxopropionate which comprises:

reacting 2,5,6-trihalo-3-cyanopyridine with ethyl haloacetate at the presence of a transition metal in powder in anhydrous solvent; and treating the resulting solution with HCl.

2. The process as defined in claim 1, wherein said anhydrous solvent is anhydrous tetrahydrofuran (THF) or anhydrous diethyl ether.

3. The process as defined in claim 1, wherein said transition metal is selected from the group consisting of Mg, Zn, Sn, Pb, Cu, Ag, Ni and Co.

4. The process as defined in claim 1, wherein ethyl haloaceate is selected from the group consisting of ethyl chloroacetate, ethyl bromoacetate, and ethyl iodoacetate.

5. A process for preparing ethyl 3-(2,5,6-trihalopyridin-3-yl)-3-oxopropionate from 2,5,6-trihalo-3-cyanopyridine, which comprises:

heating 2,5,6-trihalo-3-cyanopyridine and a transition metal in powder in anhydrous solvent to the boiling point;

reacting 2,5,6-trihalo-3-cyanopyridine with ethyl haloacetate by adding ethyl haloacetate dropwise to the resulting solution;

cooling the resulting solution to about 10° C.;

adding concentrated HCl and distilled water to the resulting solution during agitation thereof; and filtering the product.

6. The process as defined in claim 5, wherein said heating step comprises adding the transition metal powder activated at 0–30° C. and 2,5,6-trihalo-3-cyanopyridine to a reactor, keeping the reactor under reduced pressure or vacuum to evaporate moisture and solvent, filling with nitrogen gas therein, and heating the resulting solution to the boiling point.

7. The process as defined in claim 5, wherein said reacting step comprises adding the ethyl haloacetate dropwise over about 1 hour to about 3 hours, and refluxing the resulting solution for about 30 minutes to about 1 hour further to react THCP with the ethyl haloacetate.

8. The process as defined in claim 5, wherein said adding step further comprises agitating the resulting solution for about 2 hours.

9. The process as defined in claim 5, wherein said ethyl 3-(2,5,6-trihalopyridin-3-yl)-3-oxopropionate is prepared in a yield of about 90% or more.

10. The process as defined in claim 5, further comprising recrystallizing the filtrate after filtering.

11. The process as defined in claim 10, wherein said recrystallizing step comprises washing the unpurified ETPO within short time by putting into solvent, putting the washed ETPO into solvent, heating the resulting solution to 60° C. to dissolve the washed ETPO, distilling the solvent, and quenching the product.

12. The process as defined in claim 10, wherein said ethyl 3-(2,5,6-trihalopyridin-3-yl)-3-oxopropionate is prepared in a yield of about 97% or more.

13. The process as defined in claim 5, wherein said anhydrous solvent is anhydrous tetrahydrofuran (THF) or anhydrous diethyl ether.

14. The process as defined in claim 5, wherein said transition metal is selected from the group consisting of Mg, Zn, Sn, Pb, Cu, Ag, Ni and Co.

15. The process as defined in claim 5, wherein ethyl haloaceate is selected from the group consisting of ethyl chloroacetate, ethyl bromoacetate, and ethyl iodoacetate.

* * * * *